(12) United States Patent
Thornhill et al.

(10) Patent No.: US 7,191,673 B2
(45) Date of Patent: Mar. 20, 2007

(54) APPARATUS FOR INSPECTING A LATERAL CONDUIT

(75) Inventors: Bruce Thornhill, Newmarket (CA); Binh Ha, Toronto (CA)

(73) Assignee: Hathorn Corporation, Richmond Hill (CA)

( * ) Notice: Subject to any disclaimer, the term of this patent is extended or adjusted under 35 U.S.C. 154(b) by 374 days.

(21) Appl. No.: 10/637,580

(22) Filed: Aug. 11, 2003

(65) Prior Publication Data

US 2005/0034544 A1 Feb. 17, 2005

(51) Int. Cl.
*G01M 19/00* (2006.01)

(52) U.S. Cl. .................................... 73/865.8

(58) Field of Classification Search ............. 73/865.8, 73/866.5, 623, 784, 81–84, 864.74; 356/241.1, 356/241.3, 241.4, 241.6; 348/84, 85; 324/220
See application file for complete search history.

(56) References Cited

U.S. PATENT DOCUMENTS

| | | | |
|---|---|---|---|
| 4,265,608 A * | 5/1981 | Tunador et al. | 425/149 |
| 4,651,558 A | 3/1987 | Martin et al. | |
| 4,677,472 A | 6/1987 | Wood | |
| RE33,160 E | 2/1990 | Guthrie et al. | |
| 4,991,006 A | 2/1991 | Wood | |
| 5,370,006 A | 12/1994 | Zollinger et al. | |
| 5,385,049 A | 1/1995 | Hunt et al. | |
| 5,721,386 A * | 2/1998 | Marette | 73/865.8 |
| 5,956,135 A | 9/1999 | Quesnel | |
| 5,992,247 A * | 11/1999 | Manestar | 73/865.8 |
| 6,357,310 B1 * | 3/2002 | Blanchet et al. | 74/89.21 |
| 6,505,525 B2 | 1/2003 | McGrew | |
| 6,575,862 B2 * | 6/2003 | Miyaji | 474/205 |

FOREIGN PATENT DOCUMENTS

CA 2309018 5/2000

OTHER PUBLICATIONS

Sewer Depot Inc., Lateral Navigator, Copyright 1999-2003, 4 pages. www.sewerdepot.com/Product/Quesnel%20and%20Assoc/cameras/lateral%20navigator/lateral_navigator.html, dated Jul. 7, 2003.
Aries Industries, Inc., Lateral Inspection Systems, Copyright 2003 Aries Industries Inc., 6 pages. www.ariesind.com/lateral.html, dated Jul. 7, 2003.
Leif M. Jensen Kloakservice, www.aj-lmj.dk/english/main.htm, 4 pages, dated Jul. 7, 2003.
Cues Inc., Lamp Self-Propelled Lateral and Mainline Probe, www.cuesinc.com/LAMP.htm, 2 pages, dated Jul. 7, 2003.

* cited by examiner

*Primary Examiner*—Robert Raevis
(74) *Attorney, Agent, or Firm*—Bereskin & Parr

(57) ABSTRACT

An apparatus for inspecting a lateral conduit from a main conduit including a frame, an upper push rod drive assembly and a lower push rod drive assembly. The upper push rod drive assembly includes an upper track having a plurality of upper attachments mounted thereto for engaging the push rod. The lower push rod drive assembly includes a lower track having a plurality of lower attachments mounted thereto for engaging the push rod. The push rod is held between the upper and lower attachments and in a preferred embodiment, some of the upper attachments, some of the lower attachments and the push rod move with a linearly synchronized motion.

22 Claims, 7 Drawing Sheets

APPARATUS FOR INSPECTING A LATERAL CONDUIT

FIELD OF THE INVENTION

This invention relates to an apparatus for inspecting lateral sewer and drain pipes or conduits. More particularly, the invention relates to a mechanism for controlling the extension and retraction of a push rod of such apparatuses.

BACKGROUND OF THE INVENTION

A wide variety of apparatuses have been developed for inspecting the interior of a lateral conduit for maintenance concerns, such as cracks and leaks. Typically, these apparatuses include a push rod, a push rod drive assembly and a camera mounted to the push rod. The apparatus can be remotely guided into a main conduit. The apparatus is advanced into the main conduit and positioned near a junction with a lateral conduit. The push rod and camera are then extended into the lateral conduit using the drive assembly to allow an inspector to view the interior of the conduit on a remote monitor coupled to the camera. When the lateral conduit has been inspected, the push rod and camera are retracted and the apparatus may be moved to the location of another lateral conduit or may be withdrawn from the main conduit.

A problem that occurs with the use of these types of apparatuses is that the push rod drive assembly pierces or otherwise damages the surface of the push rod. Usually this occurs because the push rod drive assembly applies excessive pressure to the surface of the push rod as it is extended and retracted. It may also occur because the push rod drive assembly becomes dirty with debris and then pushes and scrapes the debris against the surface of the push rod.

Accordingly, there is a need for a lateral conduit inspection apparatus that reduces damage to the surface of a push road during use of the apparatus.

SUMMARY OF THE INVENTION

The invention is directed to an apparatus for inspecting a lateral conduit from a main conduit. The apparatus comprises a frame, a push rod transport motor and a push rod drive assembly. The push rod drive assembly has an upper push rod drive assembly and a lower push rod drive assembly.

The upper push rod drive assembly includes an upper track that travels around an upper drive pulley and an upper idler pulley. The upper drive pulley is coupled to the push rod transport motor and is responsive to the push rod transport motor to move the upper track. A plurality of upper attachments are attached to the upper track. When a push rod is inserted into the apparatus, some of the upper attachments contact the push rod.

The lower push rod drive assembly has a lower track that travels around a lower drive pulley and a lower idler pulley. The lower drive pulley is coupled to the push rod transport motor through an interlocking with the upper drive pulley. Alternatively, the lower drive pulley could be connected to the push rod drive motor independently of the upper drive pulley. The lower track moves under the control of the lower drive pulley in response to the push rod drive motor. A plurality of lower attachments are attached to the low track and when a push rod is inserted into the apparatus, some of the lower attachments contact the push rod.

In one embodiment of the present invention, the upper and lower attachments in contact with the push rod are positioned in complementary pairs the contact the same section of the push rod on opposing sides. In other embodiments, the upper and lower attachments may contact different sections of the push rod, or may contact alternating sections of the push rod.

Preferably, the movement of the upper and lower attachments is synchronized by interlocking the upper and lower drive pulleys.

The upper and lower attachments frictionally hold the push rod so that the push rod moves in linear synchronization with the upper and lower attachments when the upper and lower tracks are moved under the control of the push rod transport motor. Since a plurality of upper and lower attachments frictionally hold the push rod at any time, a greater surface area contact may be created between the attachments and the push rod, allowing the push rod to be extended or retracted with greater force or with less force at any particular part of the push rod, or both.

The upper and lower attachments may have various profiles on their push rod engaging faces. In embodiment, the upper attachments have an arced profile, which may include up to 180 degrees of arc and which is sized to complement the outer diameter of the push rod. The lower attachments are ribbed. In other embodiments, both the upper and lower attachments may have an arced or semicircular profile, or both may be ribbed, or they may have a compound surface with two or more surfaces for engaging the push rod. In other embodiments, a mixture of upper or lower attachments, or both, with different profiles and shapes may be used.

In one embodiment of the invention, the upper push rod drive assembly includes an upper slide bar with an upper pressure surface that supports the upper attachments against the push bar. The lower push rod drive assembly includes a lower slide bar with a lower pressure surface that is biased towards the push rod to press the lower attachments against the push rod. The upper and lower slide bars hold the push bar tightly between the upper and lower attachments.

In one embodiment, the upper and lower tracks are metal chains. In that embodiment, the upper and lower pressure surfaces are made of a ceramic impregnated metal to provide a low friction and long wearing pressure surface.

In other embodiments, the upper track or the lower or both may be belts or other forms of tracks. In such cases the upper and lower pulleys and the upper and lower pressure surfaces will be chosen to complement the nature of the track.

BRIEF DESCRIPTION OF THE DRAWINGS

For a better understanding of the present invention and to show clearly how it may be carried into effect, reference will now be made, by way of example, to the accompanying drawings which show a preferred embodiment of the present invention, in which.

DETAILED DESCRIPTION OF EXEMPLARY EMBODIMENT

Figure 1:
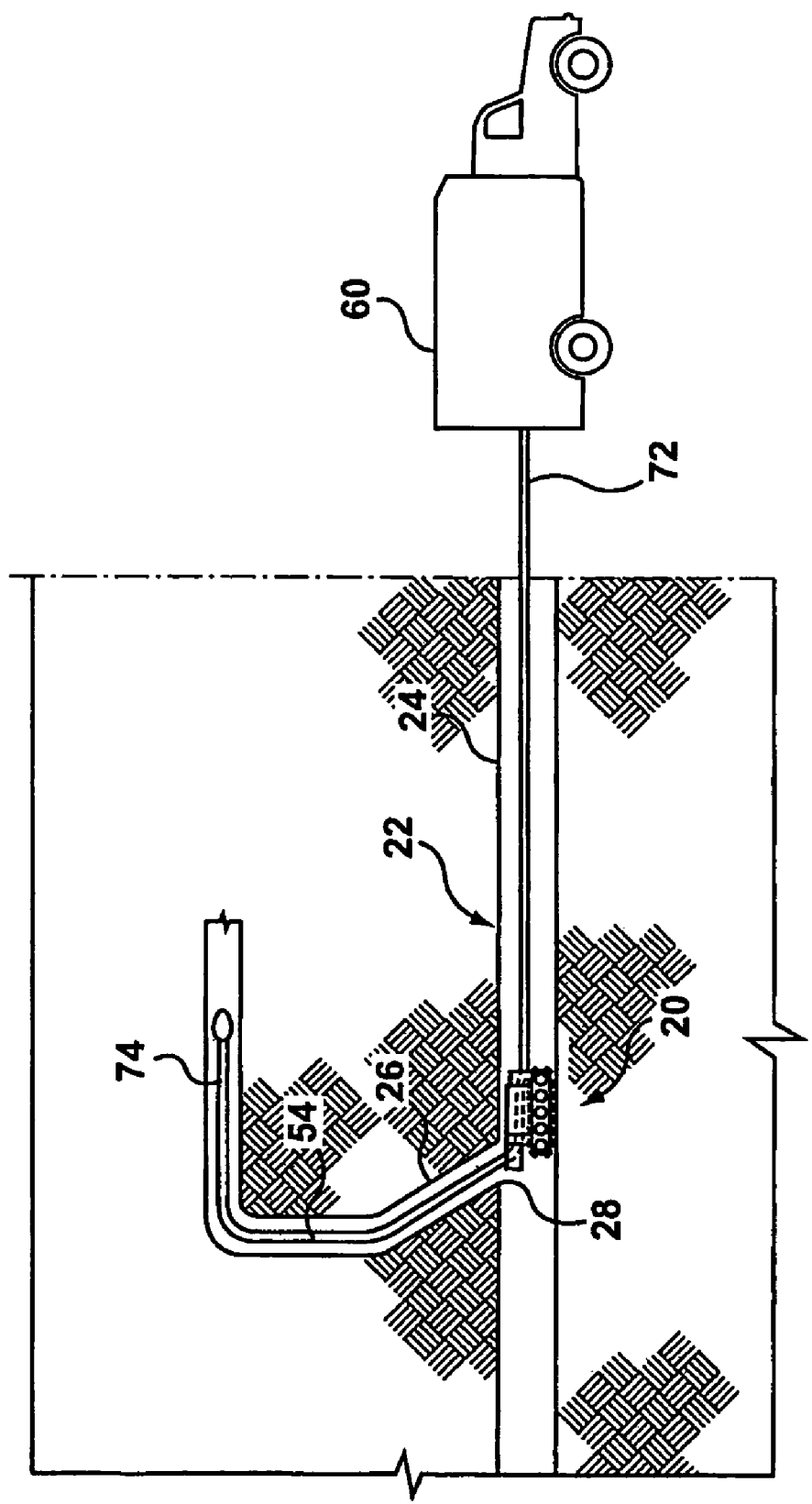
FIG. 1 is a side elevation view of the apparatus of the present invention disposed in a conduit system.

Reference is first made to FIG. 1, which illustrates an inspection apparatus 20 made in accordance with a first exemplary embodiment of the invention. Apparatus 20 is positioned inside a conduit system 22 comprising a main conduit 24, a lateral conduit 26 and a junction 28. Apparatus 20 is adapted for inspecting at least a portion of lateral conduit 26 extending from main conduit 24 to determine whether any maintenance of conduit system 22 is required. Various types of maintenance concerns may be revealed during inspection of conduit system 22, such as, for example, obstructions, insufficient flow capacity or discontinuities in the interior surface of lateral conduit 26.

Figure 2:
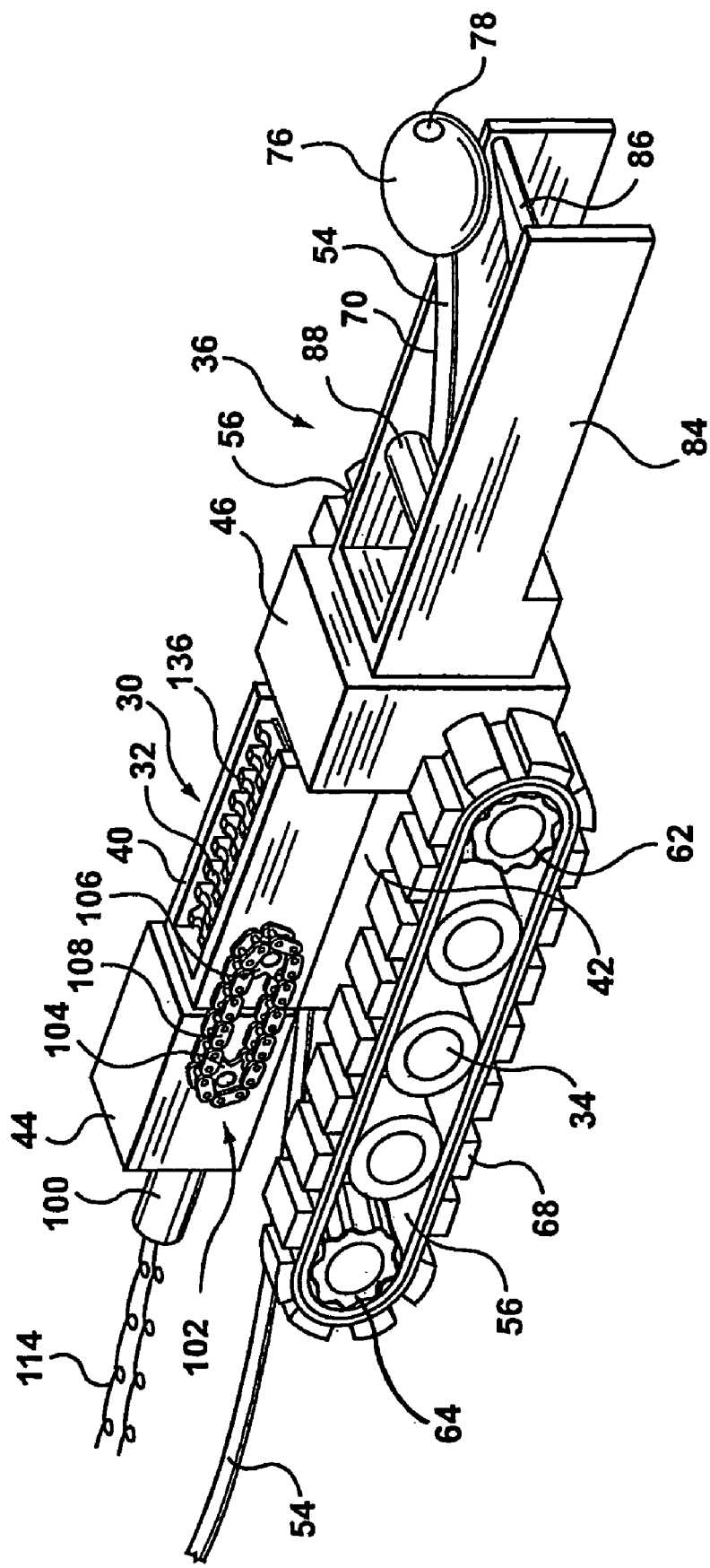
FIG. 2 is a side elevation view of the apparatus of FIG. 1.

Reference is made to FIG. 2. Apparatus 20 comprises a frame 30, a push rod drive assembly 32, a propulsion mechanism 34 and a deflector assembly 36.

Frame 30 includes an upper frame section 40, a lower frame section 42, and frame sections 44, 46. Frame 30 will typically include cover members (not shown) that protect the components of apparatus 20 from debris and other intrusions. Frame 30 may be made from any suitable material, such as metals or plastics.

Push rod drive assembly 32 includes an upper push rod drive assembly 50 that is generally assembled in upper frame section 40 and a lower push rod drive assembly 52 that is generally assembled within lower frame section 42. Push rod drive assembly 32 is used to extend and retract a push rod 54 into or from a lateral conduit 26 (FIG. 1).

Propulsion mechanism 34 is mounted to frame 30. Propulsion mechanism 34 is used for advancing and reversing apparatus 20 within main conduit 24 (FIG. 1). Propulsion mechanism 34 includes at least one traction means 56 coupled to a propulsion motor (not shown) that controls the operation of traction means 56 and thereby the advancement or reversal of apparatus 20 in main conduit 24. The propulsion motor may be an electrical motor, a hydraulic motor or a gas driven motor (for example, an air powered motor or a motor powered by an inert gas such as helium). Electrical power, hydraulic fluid or gas for the propulsion is controllably supplied by supply lines (not shown) that extend to a remote location 60 (FIG. 1). Remote location 60 may be located in an inspection truck or provided in a compact instrument that can be carried by an inspector.

In this exemplary embodiment, traction means 56 includes a chain 66 that travels around sprockets 62 and 64. Typically one or both of sprockets 62 and 64 will be driven by the propulsion motor. Chain 66 has friction pads 68 that frictionally engage main conduit 24 to move apparatus 20 within main conduit 20. Such movement is controlled by the propulsion motor, which is in turn controlled from remote location 60 through control lines (not shown).

It will be appreciated that traction means 56 may include wheels, belts or any other suitable moveable member that can contact the interior surface of main conduit 24. Alternatively, it will be noted that apparatus 20 may be manually positioned within main conduit 24 by various means, including, for example, rolling the apparatus along main conduit 24.

The mounting, design and use of the propulsion mechanism is well known to those familiar with devices for inspecting lateral sewer conduits and is not further described here.

Push rod 54 comprises an outer sheath 70 and a rigid core (not shown). Push rod 54 has a proximal end 72 (FIG. 1) and a distal end 74 (FIG. 1). Distal end 74 that is advanced into lateral conduit 26 using apparatus 20. The rigid core material having sufficient longitudinal compressive rigidity so that push rod 54 resists buckling when it is advanced into lateral conduit 26. This is of particular benefit when push rod 54 encounters an obstruction within lateral conduit 26. A push rod having the desired longitudinal compressive rigidity may be capable of advancing beyond the obstruction to allow an inspector to determine what additional repairs to lateral conduit 26 may be necessary.

The core must also have sufficient transverse flexibility to enable push rod 54 to be advanced around bends within lateral conduit 26. Various push rods are known in the art and a skilled person will be capable of selecting a push rod suitable for the nature of a particular conduit system 22 (FIG. 1).

An inspection device 76 is mounted to distal end 74 of push rod 54 for remotely inspecting the interior of lateral conduit 26. In this exemplary embodiment, inspection device 76 includes a camera 78. Push rod 54 includes cables within its sheath to provide power and control signals to camera 78 and to transmit images captured by camera 78 to remote location 60. Camera 78 may be provided with a light and a lens, as is known in the art. In other embodiments of the invention, inspection device 76 may be or may include an ultrasonic probe for determining the location of cracks in the interior of lateral conduit 26. In other embodiments, the inspection may be or may include a device that emits a radio frequency or audible signal to permit the inspection device's position in conduit system 22 to be determined.

Referring briefly to FIG. 1, a lateral conduit 26 may extend from main conduit 24 at any angle provided that fluid can flow from lateral conduit 26 into main conduit 24 under the flow of gravity or in some cases, under the force of a pump. Accordingly, it may be necessary to guide inspection device 76 and push rod 54 in various different directions to allow inspection device 76 to enter lateral conduits at different angles.

Figure 3:
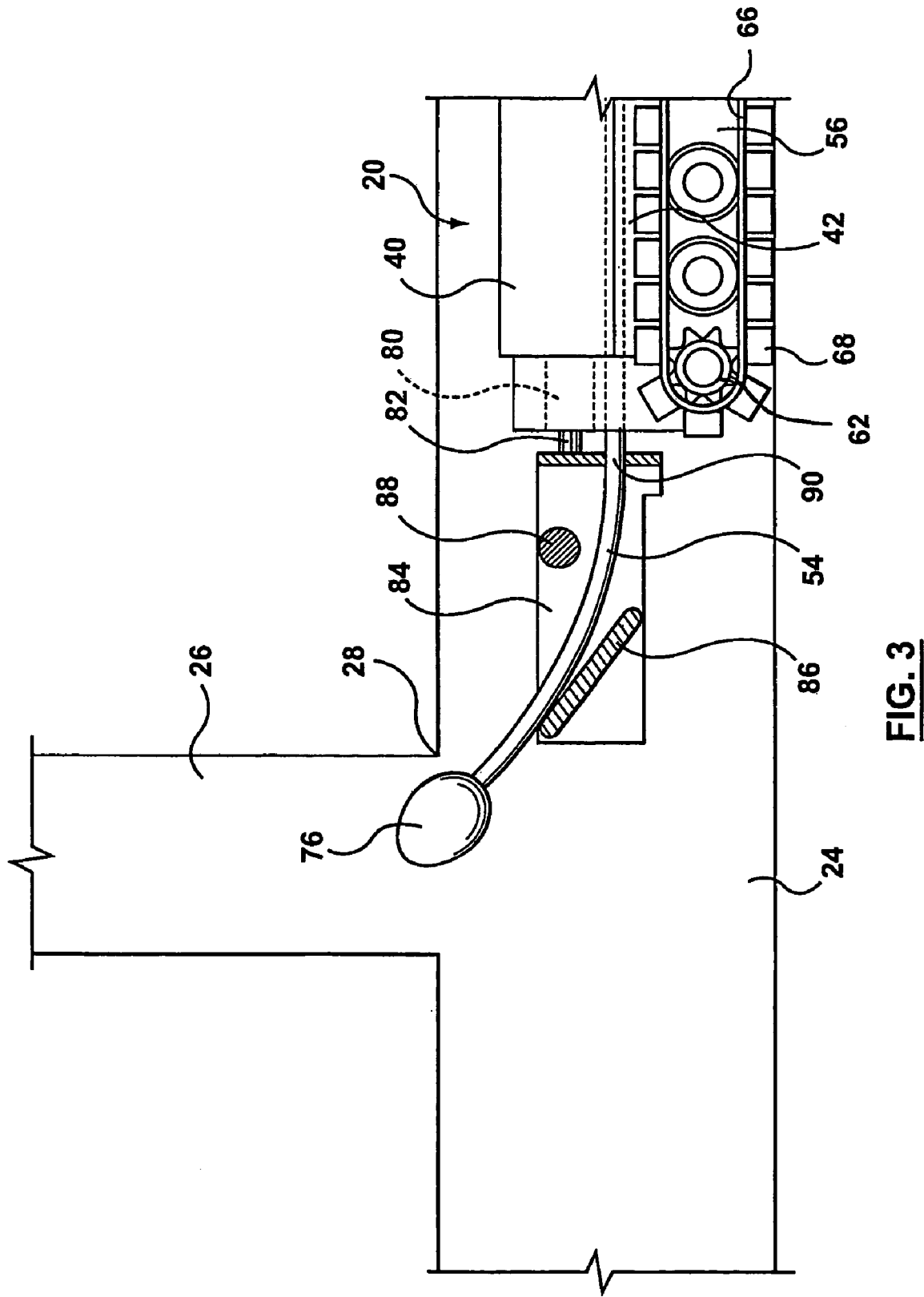
FIG. 3 is a side elevation view of the apparatus of FIG. 1 with a partial sectional view illustrating a deflector assembly of the apparatus.

Referring to FIGS. 2 and 3, deflector assembly 36 includes a deflector motor 80, a deflector frame 84 and a deflector plate 86. Deflector assembly is shown in cross section in FIG. 3. Deflector motor 80 is mounted in frame 30 of apparatus 20. Deflector frame 84 is coupled to deflector motor 80 through a coupling 82. Deflector plate 86 is mounted in deflector frame 84 at an angle to the longitudinal direction of apparatus 20 and of push rod 54 as it passes through push rod drive assembly 32. Deflector frame 84 is rotated by deflector motor 80, based on control signals received from remote location 60 through control lines (not shown). As deflector frame 84 is rotated, deflector plate 86 is similarly rotated.

Push rod 54 extends from push rod drive assembly 32 through an orifice 90 in deflector frame 84. Orifice 90 is shaped to permit push rod 54 to pass through it when deflector frame 84 is rotated. Alternately, deflector frame 84 may be shaped to permit push rod 54 to pass through to deflector plate 86 without passing through an orifice in the wall of frame 84. When push rod 54 is sufficiently extended from frame 30 of apparatus 20, inspection device 76 strikes deflector plate 86 and is deflected in a different direction depending on the angle of deflector plate 86. By first positioning apparatus 20 adjacent to junction 28 between a main conduit 24 and a lateral conduit 26, rotating deflector frame 84 and deflector plate 86 to an appropriate direction and then extending push rod 54, push rod 54 is directed into lateral conduit 26, as shown in FIG. 3.

Deflector assembly 36 may optionally be provided with a roller bar 88. Roller bar 88 limits the degree to which push rod 54 may be forced to bend as it emerges from apparatus 20, thereby reducing the chance of the push rod breaking.

Figure 4:
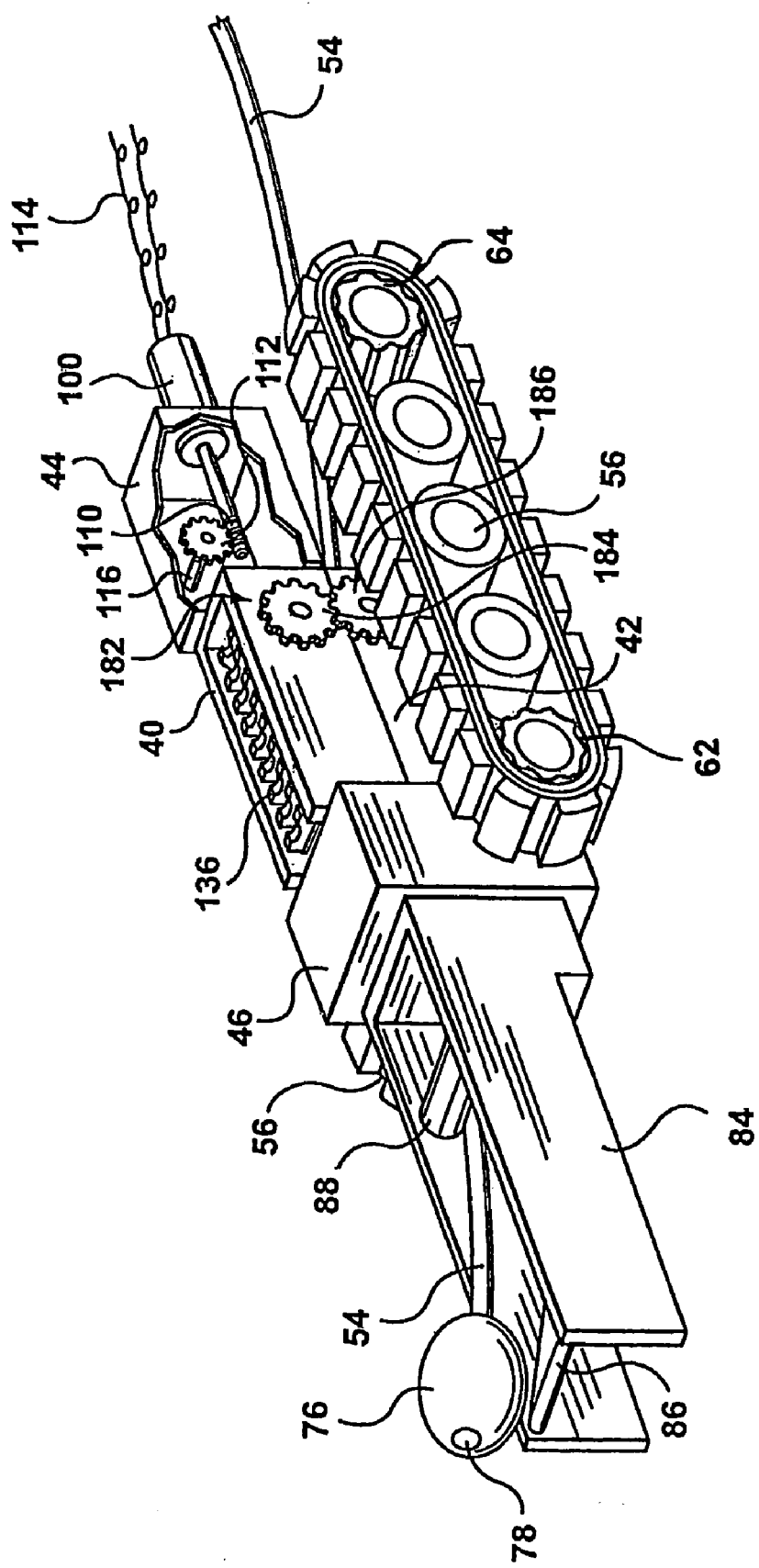
FIG. 4 is a side elevation view of the apparatus of FIG. 1, taken from the opposite of the view of FIG. 2, with a partial section view illustrating a push rod transport motor of the apparatus.
Figure 5:
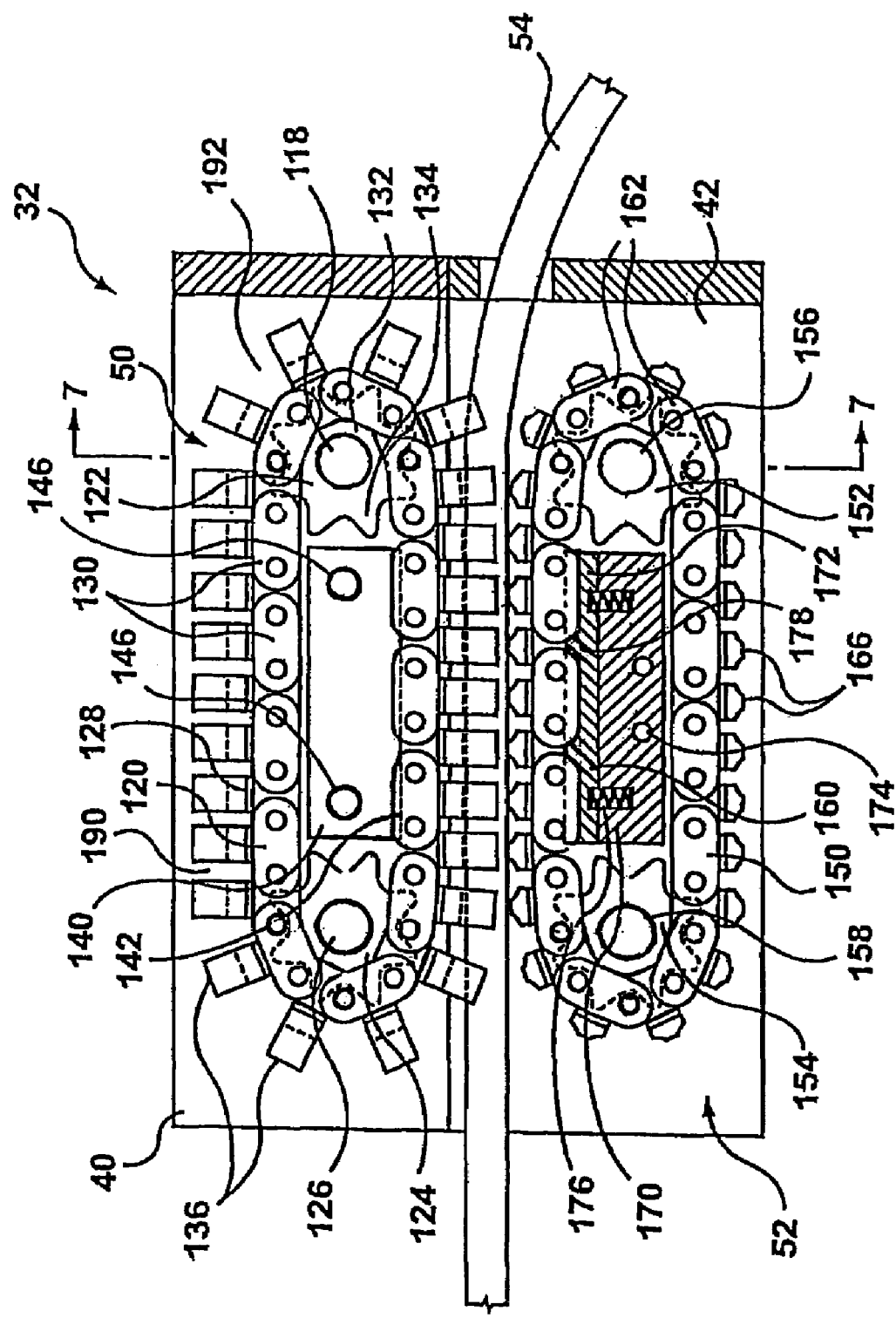
FIG. 5 is an isolated view of an upper push rod drive assembly and a lower push rod drive assembly of the apparatus of FIG. 1.
Figure 6:
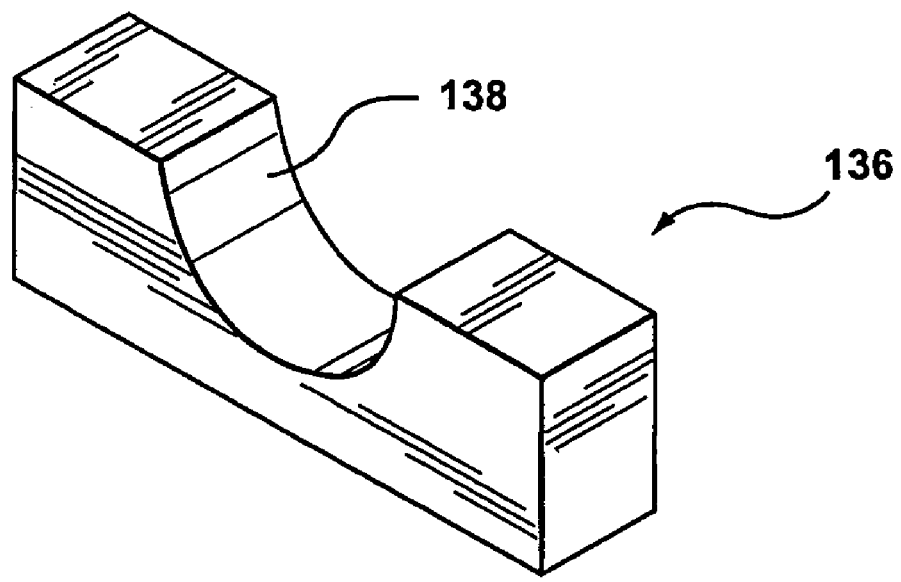
FIG. 6 is an isolated view of an upper attachment of the apparatus of FIG. 1.
Figure 8:
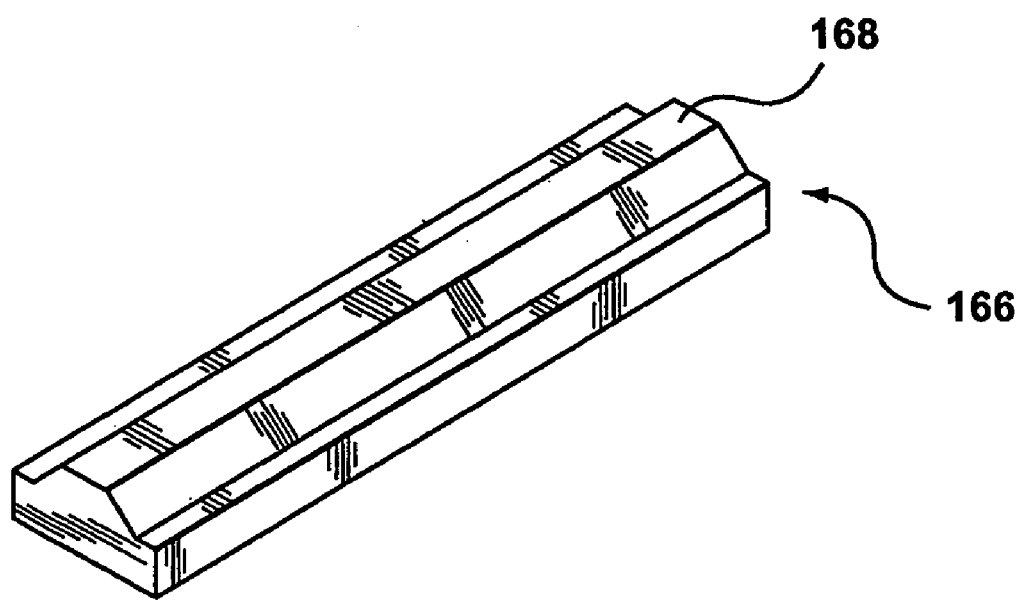
FIG. 8 is a isolated view of a lower attachment of the apparatus of FIG. 1.

Referring to FIGS. 2, 4 and 5, push rod drive assembly 32 comprises an upper push rod drive assembly 50, a lower push rod drive assembly 52, a push rod transport motor 100 and a drive coupling 102. Push rod transport motor 100 is mounted to frame section 44 and may be an electrical, hydraulic or gas power motor. Electrical power and control signals or hydraulic fluid or gas are supplied, typically from remote location 60, to push rod transport motor 100 through control or supply lines 114. Drive coupling 102 includes a drive sprocket 104, a driven sprocket 106 and a chain 108. Drive sprocket 104 is mounted on a shaft 116 that is rotatably mounted to frame section 44. Driven sprocket is mounted on an upper drive shaft 118 that is rotatably mounted in upper frame section 40. Motor 100 may drive the drive sprocket 104 directly or through a linkage. In the present embodiment, motor 100 and driver sprocket 104 are linked through a worm gear 110 mounted to the shaft of motor 100 and a transfer gear 112 (illustrated in the cutaway portion of FIG. 4). Transfer gear 112 and drive sprocket 104 are fixedly mounted to a common shaft so that drive sprocket 104 rotates in response to rotation of worm gear 110. Chain 108 links drive sprocket 104 and driven sprocket 106 so that motor 100 controls the rotation of driven sprocket 106. Motor 100 is controlled from remote location 60 (FIG. 1) through control lines 114.

Upper push rod drive assembly 50 is generally assembled within and around upper frame section 40. Upper push rod drive assembly 50 includes an upper track 120 that travels around an upper drive pulley 122 and an upper idler pulley 124 and an upper slide bar 140. Upper drive pulley 122 and upper idler pulley 124 are mounted to upper frame section 40. Upper drive pulley 122 and driven sprocket 106 are fixedly and commonly mounted on upper drive shaft 118 so that the rotation of drive pulley 122 is controlled by motor 100. Upper idler pulley is mounted on an upper idler shaft 126.

Upper track 120 may be any suitable continuous belt or chain. In the present embodiment, upper track 120 is a chain comprising a plurality of upper chain sections 130 which are each pivotally interconnected with the next adjacent sections 130 in known manner. Alternatively, the upper track may be a metal, plastic, rubber, rubberized or other type of belt.

In the present embodiment, upper drive pulley 122 is a sprocket with a base portion 132 and a plurality of teeth 134 that positively engage chain section 130 of upper track 120 to drive the movement of upper track 120 in response to motor 100. In other embodiments, upper drive pulley 122 may frictionally engage track 120, particularly in an embodiment where track 120 is a belt made of a sheet material.

Reference is made to FIGS. 2, 5, 6 and 7. A plurality of upper attachments 136 are mounted-adjacent the outer side 128 of upper track 120. In the present embodiment, one attachment 136 is mounted at the coupling of each adjacent pair of upper chain sections 130. In other embodiments, attachments may be mounted to some or all of the chain sections, or may be mounted to the upper track using fastening devices suitable for the nature of the upper track.

Each of the upper attachments 136 has a push rod engaging surface 138. Push rod engaging surface 138 has a generally semi-circular profile to conform to a portion of the outer surface of push rod 54. The radius of push rod engaging surface 138 is slightly larger that the outer radius of push rod 54. In other embodiments of the present invention, push rod engaging surface 138 may have a different shape.

In another embodiment, the profile of push rod engaging surface 138 may be an arc extending over up to 180 degrees. In another embodiment, push rod engaging surface 138 may have an elliptical profile, which may be more easily used with push rods of different outer diameters. In another embodiment, push rod engaging surface 138 may have a multi-faceted surface composed of a plurality of flat faces, some or all of which contact push rod 54 when apparatus 20 is assembled. In other embodiments, attachments with differently shaped push rod engaging surfaces may be used together.

Upper slide bar 140 is mounted in upper frame section 40 between upper drive pulley 122 and upper idler pulley 124 using mounting holes 146. Upper slide bar 140 has an upper pressure surface 142 that is positioned against upper track 120 to maintain a plurality of upper attachments 136 in contact with push rod 54. Upper slide bar 140 may be made of a metal, such as steel, stainless steel, bronze, aluminum or another metal, plastic material or other suitable material, depending on the nature of upper track 120. In the present embodiment, in which upper track 120 is a metal chain, the upper pressure surface is formed of a ceramic impregnated metal slide bar to provide a low friction and long wearing surface for the chain to slide over.

Reference is made to FIGS. 4, 5, 7 and 8 which illustrate lower push rod drive assembly 52. Lower push rod assembly 52 comprises a lower frame section 42, a lower track 150 that travels around a lower drive pulley 152 and a lower idler pulley 154 and a lower slide bar 160. Lower drive pulley 152 and lower idler pulley 154 are mounted in lower frame 42 respectively on lower drive shaft 156 and lower idler shaft 158. Like upper track 120, lower track 150 may be any suitable belt or chain. In this embodiment, lower track 150 is also a chain comprising a plurality of lower chain sections 162 pivotally connected to adjacent chain sections. A plurality of lower attachments 166 are mounted adjacent the outer side 164 of lower track 150. Each of the plurality of lower attachments 166 has a push rod engaging surface 168 that engages push rod 54. Push rod engaging surface 168 may have any suitable profile for engaging push rod 54. In the present embodiment, push rod engaging surfaces 168 are ribs with a flat surface for engaging push rod 54. In other embodiments, push rod engaging surfaces 168 may be ribs with a rounded or curved surface, or they may have the semi-circular profile like that of upper attachments 136, as is discussed further below. Alternatively, the lower attachments may have one of the profiles described above in relation to upper attachments or may have a mixture of profiles.

Lower slide bar 160 is comprised of a mounting bar 170 and a lower pressure bar 172, which are shown in cross section in FIG. 5. Mounting bar 170 is mounted in lower frame section 42 between lower drive pulley 152 and lower idler pulley 154 using mounting holes 174. Lower pressure bar 172 is mounted on mounting bar 170 with a pair of compression springs 176 between them. Springs 176 bias a lower pressure surface 178 of lower pressure bar 172 against lower track 150, thereby biasing a plurality of lower attachments 166 towards push rod 54. The pressure applied by lower pressure bar 172 to push rod 54 also holds push rod 54 tightly against upper attachments 186. In the present embodiment, lower pressure surface 178 is formed of a ceramic impregnated metal, like upper pressure surface 142. In other embodiments, lower pressure bar 172 may be formed of any material, as described above in relation to upper slide bar 140, depending on the nature of lower track 150.

Upper slide bar 140 and lower slide bar 160 cooperate to hold push rod 54 tightly between upper attachments 136 and lower attachments 166. In this embodiment, upper slide bar 140 has been described as statically mounted in upper frame section 40, while lower slide bar 160 has been described as having springs 176 that bias lower pressure bar 172 against push rod 54. In another embodiment, upper slide bar 140 may also comprise a mounting bar and an upper pressure bar biased against the upper chain with springs or other biasing means such as an elastic material, etc.

Figure 7:
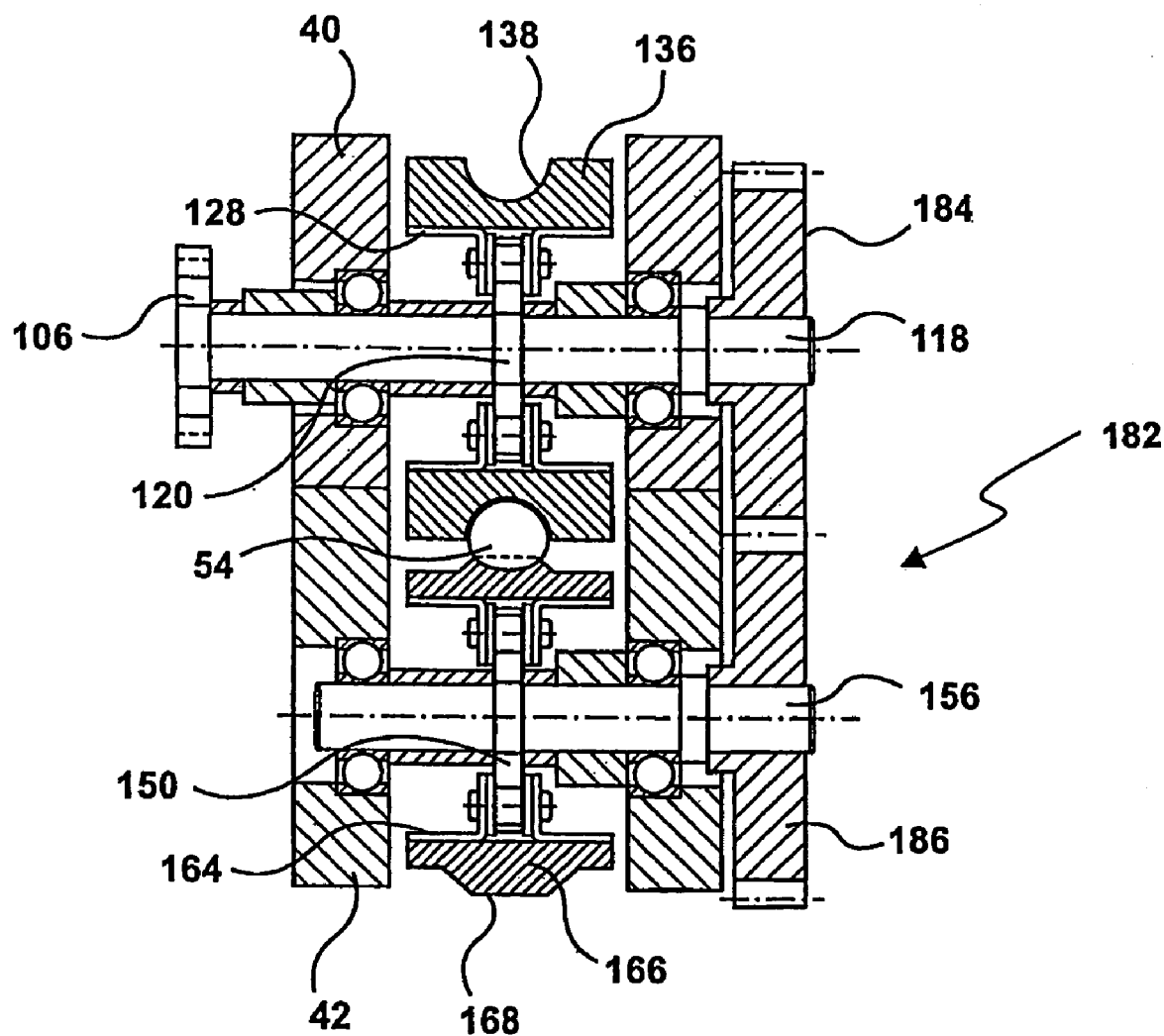
FIG. 7 is a sectional view of the upper push rod drive assembly and lower push rod drive assembly taken through the line 7—7 on FIG. 5.

FIGS. 4 and 7 illustrate a drive linkage 182 comprising an upper synchronizing gear 184 and a lower synchronizing gear 186. Upper synchronizing gear 184 is mounted on upper drive shaft 118 and rotates with driven sprocket 106 and upper drive pulley 122. Lower synchronizing gear is mounted on lower drive shaft 156 and rotates with lower drive pulley 152. Upper synchronizing gear 184 and lower synchronizing gear 186 are interlocked at drive linkage 182. Preferably, upper synchronizing gear 184 and lower synchronizing 186 are equally sized with same number of teeth so that they rotate through an identical arc in response to any movement of worm gear 110 of motor 100. This interlocks upper drive pulley 122 and lower drive pulley 152 so that they will move together. Upper drive pulley 122 and lower drive pulley 152 are preferably equally sized so that they move upper track 120 and lower track 150 the same distance in response to any movement of worm gear 110 of motor 100, thereby moving push rod 54 through apparatus 20.

In some embodiments, it may be desirable or necessary to use upper and lower synchronizing gears with different dimensions, or upper and lower drive pulleys with different dimensions, or both. In such cases, intermediate linkages or gear ratios between the components of the push rod drive assembly may be selected to ensure that the linear motion of upper track 120 and lower track 150 in the regions in which their respective attachments 136 and 166 are in contact with push rod 54 is approximately equal.

Upper push rod drive assembly 50 and lower push rod drive assembly 52 are mounted together by mounting upper frame section 40 to lower frame section 42 using fasteners (not shown) such as nuts and bolts, clips, clamps, in this position.

As shown in FIG. 5, upper push rod drive assembly 50 is positioned above lower push rod drive assembly 52 such that push rod 54 passes between some of the upper attachments 136 and corresponding lower attachments 166. Preferably, upper attachments 136 and corresponding lower attachments 166 are aligned such that they hold a section of push rod 54 directly between them, allowing the push rod to be held tightly. In other embodiments of the invention, the position of upper attachments 136 and lower attachments 166 may be staggered so that they contact alternating sections of push rod 54.

By this design, attachments 136 and 166 that are in contact with push rod 54 contact a larger total surface area of push rod 54 than prior art devices that used pulleys to directly drive the push rod. An increase surface contact area allows push rod 54 to extended and retracted with greater force. Also, a smaller radial force is required to be applied to push rod 54 at any particular point, thus reducing the extent of damage to push rod 54 and extending its useful life.

Upper and lower attachments 136 and 166 have been described as having different shapes. In another embodiment of the present invention, the upper and lower attachments have the same shape. For example, both the upper and lower attachments may the semi-circular profile shown in FIG. 6, or the rib shown in FIG. 8. The upper and lower attachments may have the various profiles described above, and may have any mixture of these and other attachments.

Reference is made to FIG. 5. As upper track 120 travels around upper drive pulley 122 and upper idler pulley 124 in response to motor 100, the spacing between adjacent attachments 136 varies. In the upper and lower flat sections of track 120 between upper drive pulley 122 and upper idler pulley 124, the spacing (shown at 190) between adjacent attachments 136 is smaller than the spacing (shown at 192) between adjacent attachments 136 at the rounded section of track 136 that are traveling around one of the upper drive pulley 122 or upper idler pulley 124. The varying spacing between adjacent attachments 136 provides a self cleaning effect, allowing some debris that collects between attachments 136 to fall away as upper track 120 travels. Similarly, the spacing between lower attachments 166 varies as they travel around lower drive pulley 152 and lower idler pulley 154, providing a similar self-cleaning effect.

In use, apparatus 20 is inserted into a conduit system 22 and controllably advanced by an operator at a remote station 60 into a main conduit 24. The operator at remote location 60 views the inside of the main conduit 24 using at least one camera 78 mounted to frame 30 of apparatus 20. In some embodiments of the present invention, a second camera may be provided in a fixed position on frame 30 for this purpose. Apparatus 20 is advanced within main conduit 24 using propulsion mechanism 34. Apparatus 20 is positioned proximate to junction 28 of main conduit 24 and a lateral conduit 26.

Deflector assembly 36 is then rotated so that camera 78 and push rod 54 will be deflected into lateral conduit 26. Push rod 54 is then extended by activating motor 100. After lateral conduit 26 has been inspected, and during the inspection, push rod 54 is retracted by engaging motor 100 in the opposite direction.

While what has been shown and described herein constitutes one exemplary embodiment of the subject invention and while some variations of the embodiment have also been described, it should be understood that various modifications and adaptions of such embodiments can be made without departing from the present invention, the scope of which is defined in the appended claims.

We claim:

1. An apparatus for inspecting a lateral conduit from a main conduit by extending and retracting a push rod into the lateral conduit, the apparatus comprising:
   a frame;
   a push rod transport motor mounted to the frame;
   an upper push rod drive assembly including an upper track;
   a plurality of upper attachments mounted to the upper track for engaging the push rod;
   a lower push rod drive assembly including a lower track;
   a plurality of lower attachments mounted to the lower track for engaging the push rod;

a drive coupling for coupling the push rod transport motor to the upper and lower push rod drive assemblies;

an upper slide bar mounted to the frame, wherein the upper slide bar includes an upper pressure surface for pressing at least some of the upper attachments against the push bar; and a lower slide bar mounted to the frame, wherein the lower slide bar includes a lower pressure surface for pressing at least some of the lower attachments against the push bar.

2. The apparatus as claimed in claim 1, wherein at least two or more of the upper attachments contact the push rod simultaneously.

3. The apparatus as claimed in claim 2, wherein the lower attachments have a rib.

4. The apparatus as claimed in claim 1, wherein a complementary pair of upper and lower attachments are positioned to contact the same section of the push rod on generally opposing sides.

5. The apparatus as claimed in claim 4, wherein at least one additional pair of complementary upper and lower attachments are positioned to contact another section of the push rod on generally opposing sides.

6. The apparatus as claimed in claim 1, wherein at least some of the upper attachment have a curved profile.

7. The apparatus as claimed in claim 1, wherein at least some of the lower attachments have a curved profile.

8. The apparatus as claimed in claim 1, wherein the upper track travels around a pair of upper pulleys mounted to the frame and wherein the spacing between adjacent upper attachments varies as the upper track travels.

9. The apparatus as claimed in claim 8, wherein the upper track is a chain comprising a plurality of pivotally connected chain sections and wherein the upper attachments are coupled to the chain and wherein the upper pulleys are sprockets.

10. The apparatus as claimed in claim 9 wherein one of the upper pulleys is an upper driven pulley coupled to the drive coupling to drive the upper track.

11. The apparatus as claimed in claim 1 wherein the upper track travels around an upper drive pulley and an upper idler pulley and the lower track travels around a lower drive pulley and a lower idler pulley and wherein the upper drive pulley moves the upper track and the lower drive pulley moves the lower track under the control of the push rod transport motor.

12. The apparatus as claimed in claim 11 wherein the upper and lower drive pulley are interlocked so that the movement of the upper and lower tracks in response to the push rod transport motor is synchronized.

13. The apparatus as claimed in claim 12, wherein the movement of push rod is linearly synchronized with the movement of at least a portion of the upper and lower tracks.

14. The apparatus as claimed in claim 1, wherein the upper track is a metal chain and wherein the upper slide bar has an upper pressure surface formed of a ceramic impregnated metal.

15. The apparatus as claimed in claim 14 wherein the lower track is a metal chain and the lower slide bar has a lower pressure surface formed of a ceramic impregnated metal.

16. The apparatus as claimed in claim 1, wherein at least some of the upper attachments and at least some of the lower attachments have a curved profile.

17. The apparatus as claimed in claim 1, wherein at least one of the upper slide bar or the lower slide bar includes a pressure bar and wherein the pressure bar is biased against the upper attachments or the lower attachments to press the upper attachments or the lower attachments against the push bar.

18. The apparatus as claimed in claim 1, wherein the upper slide bar includes an upper pressure bar biased against at least some of the upper attachments to press at least some of the upper attachments against the push bar.

19. The apparatus as claimed in claim 18 further including upper biasing means for biasing the upper pressure bar against the upper attachments.

20. The apparatus as claimed in claim 1, wherein the lower slide bar includes a lower pressure bar biased against at least some of the lower attachments to press at least some of the lower attachments against the push bar.

21. The apparatus as claimed in claim 20 further including lower biasing means for biasing the lower pressure bar against the lower attachments.

22. The apparatus as claimed in claim 20, wherein the upper slide bar includes an upper pressure bar biased against at least some of the upper attachments to press at least some of the upper attachments against the push bar.

* * * * *